United States Patent
Mennen

(10) Patent No.: US 9,000,215 B2
(45) Date of Patent: Apr. 7, 2015

(54) UREA PRODUCTION PROCESS CHARACTERIZED BY SHORT UREA MELT TRANSPORTATION TIME BETWEEN LAST CONCENTRATOR AND PRILLING TOWER

(75) Inventor: Johannes Henricus Mennen, Sittard (NL)

(73) Assignee: Stamicarbon B.V., Sittard (NL)

( * ) Notice: Subject to any disclaimer, the term of this patent is extended or adjusted under 35 U.S.C. 154(b) by 0 days.

(21) Appl. No.: 14/238,721

(22) PCT Filed: Aug. 17, 2012

(86) PCT No.: PCT/NL2012/050577
§ 371 (c)(1),
(2), (4) Date: Feb. 12, 2014

(87) PCT Pub. No.: WO2013/025109
PCT Pub. Date: Feb. 21, 2013

(65) Prior Publication Data
US 2014/0206902 A1    Jul. 24, 2014

(30) Foreign Application Priority Data
Aug. 17, 2011 (EP) ..................... 11177848

(51) Int. Cl.
*C07C 273/04* (2006.01)
(52) U.S. Cl.
CPC ................... *C07C 273/04* (2013.01)
(58) Field of Classification Search
None
See application file for complete search history.

(56) References Cited

U.S. PATENT DOCUMENTS 4,218,397 A * 8/1980 Konoki et al. ............. 564/68
6,084,129 A * 7/2000 Romiti ........................ 564/73

FOREIGN PATENT DOCUMENTS

EP    0891968    1/1999

OTHER PUBLICATIONS

International Search Report for PCT/NL2012/050577, mailed Oct. 31, 2012, 2 pages.

* cited by examiner

*Primary Examiner* — Brian J Davis
(74) *Attorney, Agent, or Firm* — Morrison & Foerster LLP

(57) ABSTRACT

The invention relates to a method for urea production and to a urea production plant wherein ammonia emission in the final step of forming urea prills is reduced. In the method, the concentration of a urea solution is performed in at least three consecutive concentration steps and the residence time of urea melt leaving a last concentrator to the prilling tower is minimized. This can be achieved by placing the last concentrator in adjacency with a urea melt inlet of the prilling tower, such as above the prilling tower. In this way, the ammonia emission in the prilling tower can be reduced by as much as 50% compared to the conventional urea production plants. The invention further relates to a method for reducing ammonia emission in the prilling tower of an existing urea production plant.

15 Claims, 2 Drawing Sheets

UREA PRODUCTION PROCESS CHARACTERIZED BY SHORT UREA MELT TRANSPORTATION TIME BETWEEN LAST CONCENTRATOR AND PRILLING TOWER

CROSS-REFEREENCE TO RELATED APPLICATIONS

This application is the national phase of PCT application PCT/NL2012/050577 having an International filing date of 17 Aug. 2012, which claims benefit of European patent application No. 11177848.6 filed 17 Aug. 2011. The contents of the above patent applications are incorporated by reference herein in their entirety.

FIELD OF THE INVENTION

The invention relates to the production of urea and, in particular, to the concentration of urea solutions followed by urea prilling.

BACKGROUND

Industrial processes presently used for urea production are based on the direct synthesis of urea from ammonia and carbon dioxide, according to the following overall reaction:

$$2NH_3 + CO_2 \rightarrow H_2N-CO-NH_2$$

The reaction comprises two consecutive reaction steps, wherein in the first step ammonium carbamate is formed, which is dehydrated in the second step to form urea.

The synthesis reaction leads to the formation of an aqueous solution of urea which needs to be concentrated in order to obtain a urea melt. This melt is further subjected to one or more finishing steps, such as prilling, granulating, pelletizing or compacting. In case of prilling, the urea melt is supplied to a prilling tower wherein it is sprayed from the top of the prilling column in a rising stream of air of ambient temperature in which the droplets solidify to form urea prills.

The prilling process conceals some critical problems including pollution of discharged air with ammonia. Ammonia is typically formed at a high temperature in a urea melt. During the prilling step, the air takes up the formed ammonia which is subsequently released into the atmosphere.

It is therefore desired to reduce ammonia emission in a urea plant and, in particular, to reduce ammonia emission in a prilling tower. It is further desired to be able to reduce ammonia emission of an existing urea plant with minimal alterations to the production process and equipment.

SUMMARY OF THE INVENTION

In order to better address one or more of the foregoing desires, the invention presents, in one aspect, a method for urea production in a urea production plant, comprising the steps of:

(a) urea synthesis from ammonia and carbon dioxide resulting in a urea solution, (b) concentration of the urea solution in at least three concentrating steps, yielding in a last step a urea melt, and (c) formation of urea prills from the urea melt, wherein the residence time of the urea melt during transport between a last concentrating step in (b) and step (c) is less than 20 sec.

The invention, in another aspect, relates to a urea production plant comprising a urea synthesis section, a concentrating section and a prilling tower, which concentrating section comprises at least three concentrators including a last concentrator upstream of the prilling tower, wherein a urea melt transportation line connecting a urea melt outlet of the last concentrator with a urea melt inlet of the prilling tower is arranged such as to realise a residence time of urea melt in the transportation line of less than 20 sec.

In yet another aspect, the invention relates to a method for reducing ammonia emissions in a prilling tower of an existing urea production plant, wherein the existing plant is provided with at least two concentrators and a prilling tower, said method comprising placing at least one additional concentrator between the concentrator immediately preceding the prilling tower and the prilling tower, wherein the length of a urea melt transportation line connecting a urea melt outlet of the additional concentrator with a urea melt inlet of the prilling tower is less than 60 m.

DETAILED DESCRIPTION OF THE INVENTION

Figure 1:
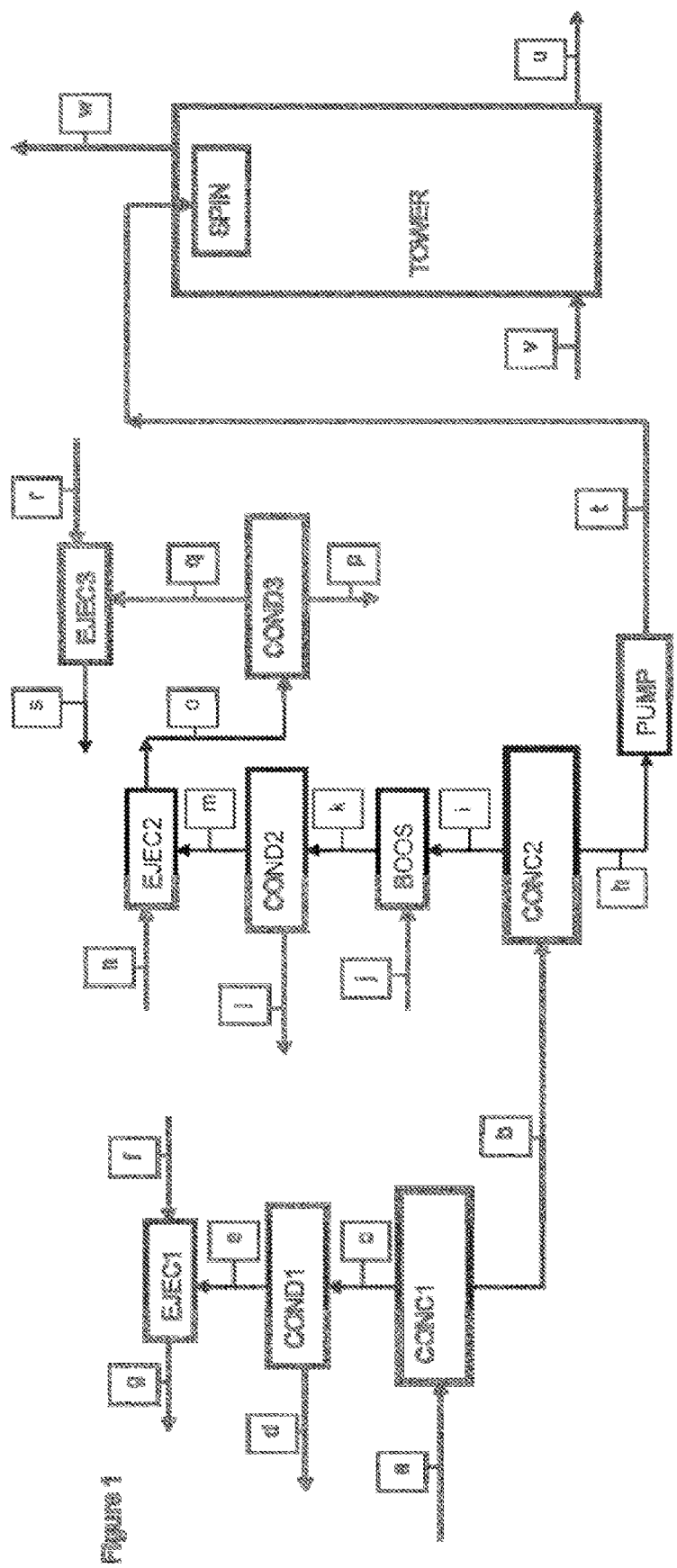
FIG. 1 is a schematic representation of an embodiment known in the art.

In a general sense, the invention is based on the judicious insight that, by limiting the residence time of a high temperature urea melt during transportation to a prilling tower, it is possible to reduce ammonia emission in the prilling tower. This can be achieved by employing at least three concentrators in a concentrating section and by bringing a urea melt outlet of a last concentrator in adjacency with a urea melt inlet of the prilling tower.

More in detail on the urea production, a typical process comprises the steps of urea synthesis from ammonia and carbon dioxide, concentration of the resulting urea solution and formation of urea prills in a prilling tower.

The synthesis of urea typically involves two reaction steps, wherein in the first step ammonium carbamate is formed, after which the ammonium carbamate is dehydrated to obtain urea. The reaction product obtained in the second step contains mainly urea, water, unbound ammonia and ammonium carbamate. The ammonium carbamate and the ammonia are removed from the solution and are generally returned to the urea synthesis zone. In addition to the above-mentioned solution in the urea synthesis zone, a gas mixture is formed which consists of unconverted ammonia and carbon dioxide together with inert gases, the so called reactor off-gas. The urea synthesis section may comprise separate zones for the formation of ammonium carbamate and urea. These zones may also be combined in a single apparatus. In urea stripping plants, the decomposition of unconverted ammonium carbamate generally takes place in one or more strippers installed downstream of the reactor, usually with the aid of a stripping gas and/or heating (thermal stripping). The gas stream leaving a stripper contains ammonia and carbon dioxide which are condensed in a high-pressure condenser and then returned to the urea synthesis zone.

After the urea synthesis, the pressure of the resulting urea solution is reduced in a urea recovery section wherein the non-converted ammonia and carbon dioxide are separated from the urea and water. The recovery section comprises usually a heater, a liquid/gas separation section and a condenser. The urea solution entering the recovery section is heated to vaporize the volatile components ammonia and carbon dioxide from the solution. The heating agent used in the heater is usually steam. The formed vapour in the heater is separated from the aqueous urea solution in the liquid/gas separation section, where after the vapour is condensed in the condenser to form a carbamate solution. The released condensation heat is usually dissipated in cooling water. The formed carbamate solution in the recovery section operated at a pressure lower than the pressure in the synthesis section is preferably returned to the urea synthesis section operating at the synthesis pressure. The recovery section is generally a single section or can be a plurality of recovery sections arranged in series.

The urea solution leaving the recovery section is then subjected to concentration in order to form a substantially anhydrous urea melt.

Typically, the concentration of the urea solution to a desired residual moisture content in the anhydrous urea melt takes place in a concentration section comprising a sequence of two concentrators. In the first concentrator the urea solution from the recovery section is typically concentrated up to 90 to 97% by weight and preferably up to 93 to 96% by weight. This concentration usually takes place at a temperature of 130 to 138° C. and a sub-atmospheric pressure of 20 to 50 kPa. The urea solution subjected to the second concentrator is concentrated to a melt with a concentration of 99.2 to 99.9% by weight and preferably to a concentration of 99.5 to 99.8% by weight. That concentration typically takes place at a temperature of 137 to 143° C. and a sub-atmospheric pressure of 2 to 5 kPa. The urea melt submitted to the following steps of forming urea solids typically has a moisture content between 0.1 to 0.8% by weight and preferably 0.2 to 0.5% by weight.

For the production of urea solids various methods are known. Prilling is a predominant method, wherein a substantially anhydrous urea melt is sprayed from the top of a prilling column in a rising stream of air of ambient temperature in which the droplets solidify to form so-called prills.

The urea melt leaving the second concentrator is usually conveyed by a pump from the last concentrator to the top of the prilling tower. On top of the prilling tower the urea melt is distributed across the circumferential area of the prilling tower by a droplet generation and distribution system such as sprayers or one or more spinning baskets. The urea droplets fall from the top of the prilling tower and solidify by exchanging heat with a rising stream of cool air that is usually introduced in the bottom of the prilling tower. The heated air is usually discharged at the top of such a prilling tower. Said prilling tower can be natural draft type characterized that the draft in the tower is encouraged by air density differences only or of a forced draft type that is characterized by using one or more air fans to support the air draft through the prilling tower. The air fans can blow the fresh air into the tower and/or the air fans can suck the warmed up air at the top of the tower into the atmosphere. The urea droplets crystallize to form prills.

In conventional urea production plants known from prior art, the urea melt transportation line between the concentrating section and the urea melt inlet of the prilling tower typically has a length between 80 to 200 m, which corresponds to a residence time of the urea melt of approximately 30 to 70 sec. This length is explained by the fact that the concentrating section typically contains bulky pieces of equipment which are therefore usually located at or near ground level. However, the urea melt inlet of the prilling tower is typically located at the top of the tower, which is the inlet to a droplet generation and distribution system such as sprayers or a spinning basket. Therefore, the urea melt leaving the last concentrator of the concentrating section must be conveyed, usually using a pump, to the top of the prilling tower. Consequently, the length of the urea melt transportation line from the last concentrator to the prilling tower is never less than the value of the height of the prilling tower.

At the same time, such a long urea melt transportation line and, hence, long residence times advance the formation of biuret in the urea melt, because of high temperatures employed especially in the last concentration step. Biuret is an organic by-product formed in urea according to the equilibrium biuret reaction:

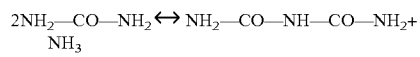

$$2NH_2-CO-NH_2 \leftrightarrow NH_2-CO-NH-CO-NH_2+ NH_3$$

The formed ammonia is transported with the urea melt to the prilling tower and is released for a major part together with the heated air discharged from the prilling tower into the atmosphere. The amount of ammonia that is typically emitted into the atmosphere from a prilling tower is about 0.5 to 1.5 kg per produced ton of product, which corresponds to more than 100 mg per normal $m^3$ of air dependent on the amount of air to be used to solidify the urea melt droplets and cooling down the prills.

In order to reduce biuret formation in the urea melt transportation line, it is therefore desired to shorten the length thereof and to reduce thereby the residence time of the urea melt. However, the bulky sizes and weights of the concentrating section including corresponding condensation and ejector equipment make it impossible to shorten the urea melt transportation line between the concentrators and the prilling tower.

According to the present invention, by using multiple concentrators it is possible to reduce the length of a urea melt transportation line from a last concentrator to the prilling tower to 60 m or less and to reduce thereby the residence time of the urea melt to 20 sec or less.

Biuret formation is inherent to urea melt transportation at high temperatures, and is especially advanced at a temperature of 138° C. or higher. Such high temperatures are typically involved in the last concentration steps where a substantially anhydrous urea melt is obtained. However, because the last concentrator is usually operated under vacuum, any ammonia formed previously in the transportation line will be separated and leave the concentrator as vapour. Hence the only critical place where ammonia can be formed causing ammonia emissions in the prilling tower is the transport line between the last concentrator and the urea melt inlet of the prilling tower. By minimising the residence time of a high temperature urea melt (such as 138° C. or higher) from the last concentrator during the transportation to the prilling tower, biuret formation and associated ammonia formation are minimised. In a preferred embodiment, the residence time of a urea melt with a temperature of 137° C. or higher is less than 20 sec and preferably less than 10 sec.

This leads to the reduction of ammonia emission in the exhaust of prilling towers by at least 50% compared to existing urea plants. Furthermore, the steam consumption used as the driving force of the ejectors in the concentrator condensation section, is reduced by at least 50% as well. The ejectors are used to obtain the necessary sub-atmospheric pressure in the concentrators. The reduced steam consumption is considered to be caused by the smaller amount of vapour released from the last evaporator in sequence.

In view of the foregoing, it is noted that the invention provides the advantage that the steam consumption to be needed for concentrating the urea solution to a urea melt can be reduced by at least 30 percent.

The invention presents, in one aspect, a method for urea production in a urea production plant. In this method, the concentration of urea is conducted in at least three concentration steps and the residence time of a urea melt obtained in a last concentration step during transport before entering a prilling tower is minimised to less than 20 sec. Preferably, said residence time is less than 15 sec, and more preferably, less than 10 sec. "Residence time during transport" means here the time spent in or on the transportation means between the last concentrator and the prilling tower. Suitably, such transportation means can be a transportation line or pipe connecting the urea melt outlet of the last concentrator with the urea melt inlet of the prilling tower. The residence time(s) in the present invention is determined as the ratio between the length of a transportation line and the average linear velocity of the flow over the cross section of the transportation line (m/s). The average linear velocity is determined by dividing the flow rate ($m^3$/s) by the cross-section of the transportation line. Suitably, the flow rate can be controlled by a pump. In practice, the diameter of a pipeline is selected based on a desired average linear velocity.

In a preferred embodiment of the invention, the concentration is conducted in three, four or five concentration steps. The use of more than six concentration steps may be less attractive from an economical and operational point of view.

In another aspect, the present invention relates to a urea production plant. The plant comprises a synthesis section, a concentrating section and a prilling tower. The concentrating section comprises at least three concentrators including a last concentrator upstream of the prilling tower. A urea melt transportation line connecting a urea melt outlet of the last concentrator with a urea melt inlet of the prilling tower is arranged such as to realise a residence time of urea melt in the transportation line of less than 20 sec. This short residence time can be suitably achieved in a transportation line with a length of less than 60 m. Preferably, said length is less than 40 m and most preferably, less than 20 m.

As follows from typical design criteria for pumping a urea melt from the evaporator to the prilling tower, a length of less than 60 m of the transportation line corresponds to a residence time of urea melt during transport in this line of less than 20 sec. The optimum design from an economic perspective is such that the best compromise between line diameter and pump capacity is achieved. Preferably the piping and the pump are designed for a maximum average linear velocity of about 5 m/s and a typical average linear velocity of about 3 m/s. At a higher velocity the required capacity of the pump becomes too high. At a velocity of 3 m/s the requirement of the residence time of urea melt in the transportation line to be less than 20 s corresponds to a length of the transport line of less than 60 m.

A typical prilling tower is at minimum about 60 meters high, typically about 80 m, although towers as high as 100 m are known. In a standard design of the prior art, the concentrators are typically placed as low as possible, for example on the ground floor. Therefore, the length of the urea melt line from the last concentrator to the prilling tower in this configuration is always more than 60 m. It is a feature of the invention to place the last concentrator as close as possible to the inlet of the prilling tower. This ensures the minimisation of the residence time of urea melt in the transport line and, consequently, a significant reduction of the emissions in the prilling tower.

In an alternative embodiment, the length of the urea melt transportation line is less than the height of the prilling tower and preferably less than a half of said height. The height can be measured from the bottom level of the prilling tower where urea solids are gathered, and vertically up to the inlet of a urea melt at the top of the prilling tower, such as the level of sprayers or a spinning basket.

A relatively short urea melt transportation line between the last concentrator and the prilling tower can advantageously be achieved by locating the last concentrator at an elevated level compared to the previous concentrators. For example, the last concentrator can be placed at any level above the previous concentrator, that is, the concentrator upstream of the last concentrator. It is further advantageous to position the last concentrator at the level of or above the level of a urea melt inlet of the prilling tower, such as on the roof of the prilling tower. In other words, when the last concentrator is provided with a urea melt outlet on a first level, and the prilling tower is provided with a urea melt inlet on a second level, the first level is preferably the same or higher than the second level. In case the last concentrator is located above the prilling tower, this has also an advantage that use can be made, at least partially, of gravitational forces to convey the urea melt to the prilling tower. From practical considerations, due to the required deep sub-atmospheric pressure in the last concentrator, it is preferred that the urea melt outlet of the last concentrator is at least 5 m, and preferably at least 8 m, higher than the urea melt inlet of the prilling tower in vertical height.

The use of at least three concentrators makes it possible to keep the last concentrator relatively small in size, such as less than a half of the volume of the previous concentrator, which in turn allows to place said last concentrator at an elevated level, for example above the previous concentrators, and preferably on or above the prilling tower. The last concentrator can be placed at an elevated level together with the corresponding equipment such as condensers and ejectors, or alone. In the latter case, the further advantage is that some of the bulky equipment can still be placed on a low level relative to the top of the prilling tower, and preferably at or near ground level, since only the position of the last concentrator with respect to the prilling tower is critical.

When placed on or above the prilling tower, for example, on the roof thereof, the length of the urea melt transportation line from the last concentrator to the sprayer or spinning basket can be minimised to preferably a maximum of 60 m, and more preferably, to a maximum of 40 m. Most preferably, the length is less than 20 m that corresponds to a residence time for urea melt in the transportation line of less than 10 sec, preferably less than 7 sec. A smaller concentrator has also a lower residence time thereby minimising the amount of biuret and ammonia formed and optimizing the removal of ammonia. In a preferred embodiment, the concentration section comprises three, four or five concentrators.

In a further aspect, the invention relates to a method for reducing ammonia emission from a prilling tower of an existing urea production plant. An existing plant is typically provided with at least two concentrators and a prilling tower. The method according to the present invention comprises placing at least one additional concentrator between a concentrator immediately preceding the prilling tower and the prilling tower, wherein the length of a urea melt transportation line connecting a urea melt outlet of the additional concentrator with a urea melt inlet of the prilling tower is less than 60 m.

The additional concentrator can have a smaller volume, such as less than a half of the volume of a previous concentrator upstream of the additional concentrator. The additional concentrator or concentrators can be placed at any height above the ground level, or above the previous concentrators. In a preferred embodiment, the urea melt outlet of the additional concentrator is at the same level or higher than the urea melt inlet of the prilling tower. More preferably, the additionally placed concentrator is positioned on or above the roof of the prilling tower. In another preferred embodiment, one, two or three additional concentrators are placed, for example, to have three, four or five concentrators in total in the concentrating section. The length of the urea melt transportation line is preferably less than 40 m and more preferably, less than 20 m. The latter corresponds to a residence time of the urea melt in said transportation line of less than 10 sec, preferably less than 7 sec. This leads to the reduction of ammonia emission in the exhaust of prilling towers by at least 50%. Furthermore, the steam consumption used as driving force of the ejectors in the concentrator condensation section, is reduced by at least 50% as well.

The present invention will further be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun, e.g., "a" or "an", "the", this includes a plural of that noun unless something else is specifically stated.

DETAILED DESCRIPTION OF THE DRAWINGS

In FIG. 1 a typical representation is given of an embodiment known in the art. In particular, FIG. 1 shows a typical sequence for concentrating a urea solution to a urea melt to be crystallized in a prilling tower as known from the prior art.

A urea solution with a concentration of typically 50 to 75% by weight of urea and a temperature of typically 60 to 90° C. is added to a concentrator (CONC1) via line (a). The concentrator (CONC1) is a shell and tube heat exchanger and the urea solution is subjected to the tube side of said concentrator. At the shell side of said concentrator steam is added to heat the solution and to evaporate the water fraction. The urea solution leaving the concentrator (CONC1) via line (b) has typically a temperature of 125 to 135° C. and is concentrated to typically 93 to 96% by weight of urea. The pressure in said concentrator is sub-atmospheric and typically between 20 to 50 kPa. The formed vapour comprising water and small amounts of ammonia and carbon dioxide is discharged from said concentrator via line (c), condensed in a condenser (COND1) and leaves said condenser as process condensate via line (d). Non-condensed vapor leaves said condenser via line (e) and is supplied to an ejector (EJEC1) to increase the pressure to atmospheric pressure. The driving force for said ejector is usually steam supplied via line (f). The steam together with the non-condensed vapor leaves said ejector via line (g) and can be released in the atmosphere but preferably is purified in the urea plant itself.

The urea solution leaving the concentrator (CONC1) via line (b) is supplied to a second concentrator (CONC2). Also this concentrator (CONC2) is typically a shell and tube heat exchanger where the urea solution is subjected to the tube side of said heat exchanger while steam is added to the shell side to heat and vaporize the volatile water fraction at sub-atmospheric pressure that is typically between 1 to 10 kPa. The temperature of the urea melt leaving said concentrator via line (h) is typically between 136 and 145° C. and comprises typically a concentration between 99.2 to 99.9% by weight of urea and biuret. The biuret increase in this concentrator is typically between 0.05 and 0.15% by weight. The major part of the formed ammonia by the biuret reaction (50 to 90%), together with the formed water vapor by the concentration leaves the concentrator (CONC2) to a booster ejector (BOOS) via line (i). The driving force for said booster ejector is steam supply via line (j). The boosted vapor leaving said booster ejector via line (k) is subjected to a condenser (COND2). The formed process condensate leaves said condenser via line (1) while the non-condensed vapor leaving said condenser via line (m) is subjected to an ejector (EJEC2). Also said ejector is driven by steam via line (n) and increases the pressure of the vapor leaving said ejector via line (o). This vapor is subjected to a next condenser (COND3) where the formed process condensate leaves said condenser via line (p) and the non-condensed inert vapor via line (q) is subjected to a next ejector (EJEC3). Also said ejector is driven by steam via line (r) and increases the pressure of the vapor discharging from said ejector to atmospheric pressure. That inert vapor is released via line (s) into the atmosphere or is preferably purified from ammonia elsewhere in the urea plant. The process condensate that leaves said condensers is collected and further processed in the urea plant to obtain clean process condensate.

The urea melt that leaves the concentrator (CONC2) via line (h) is conveyed by a pump to the sprayers or spinning basket at the top of the prilling tower via line (t). The distance between said concentrator and the spinning basket (SPIN) is generally between 80 to 200 meters dependent on the ambient air temperature to be used for cooling and crystallising the formed urea melt droplets in the prilling tower via line (u).

Since the crystallization temperature of urea melt is between 130 and 133° C., dependent on the amount of water comprised in the melt, the urea melt transportation line between the concentrator (CONC2) and the sprayers or spinning basket (SPIN) should be kept hot (130° C.). Therefore said urea melt transportation line (t) is traced or jacketed. The heating agent for keeping the urea melt transportation line hot is usually steam at a temperature of at least 130° C. Since the urea melt is kept at a temperature between 130 and 145° C. and the retention time in said urea melt line (t) is between 20 and 50 seconds, biuret is formed. Consequently ammonia is formed in that urea melt to an extent between 300 to 1000 ppm of weight at the entrance of the sprayers or spinning basket (SPIN). When the urea melt is distributed across the circumferential area of the prilling tower (TOWER), the ammonia concentration in the crystallized urea product leaving said prilling tower in line (u) is only 25 to 150 ppm by weight. For releasing the crystallization heat and cooling the solidified urea product, air is added to the prilling tower (TOWER) via line (v). The difference of the ammonia concentrations in the urea melt leaving the sprayers or spinning basket (SPIN) and the ammonia concentration in the product via line (u) is released into said air flow that is discharged from the prilling tower (TOWER) via line (w). The amount of used air in the prilling tower (TOWER) necessary to release the crystallization heat and to cool down the crystallized product determines the ammonia concentration in the air discharging from said prilling tower via line (w).

Because of the involved large sized equipment to concentrate the urea solution to a melt like the involved concentrators, condensers and booster ejector, the equipment is located on a structure that is typically on a ground level and in any case below the top of the prilling tower (TOWER). Consequently, the urea melt transportation line from a urea melt outlet of the last concentrator in series to a urea melt inlet of the prilling tower is always longer than the height of the prilling tower.

Figure 2:
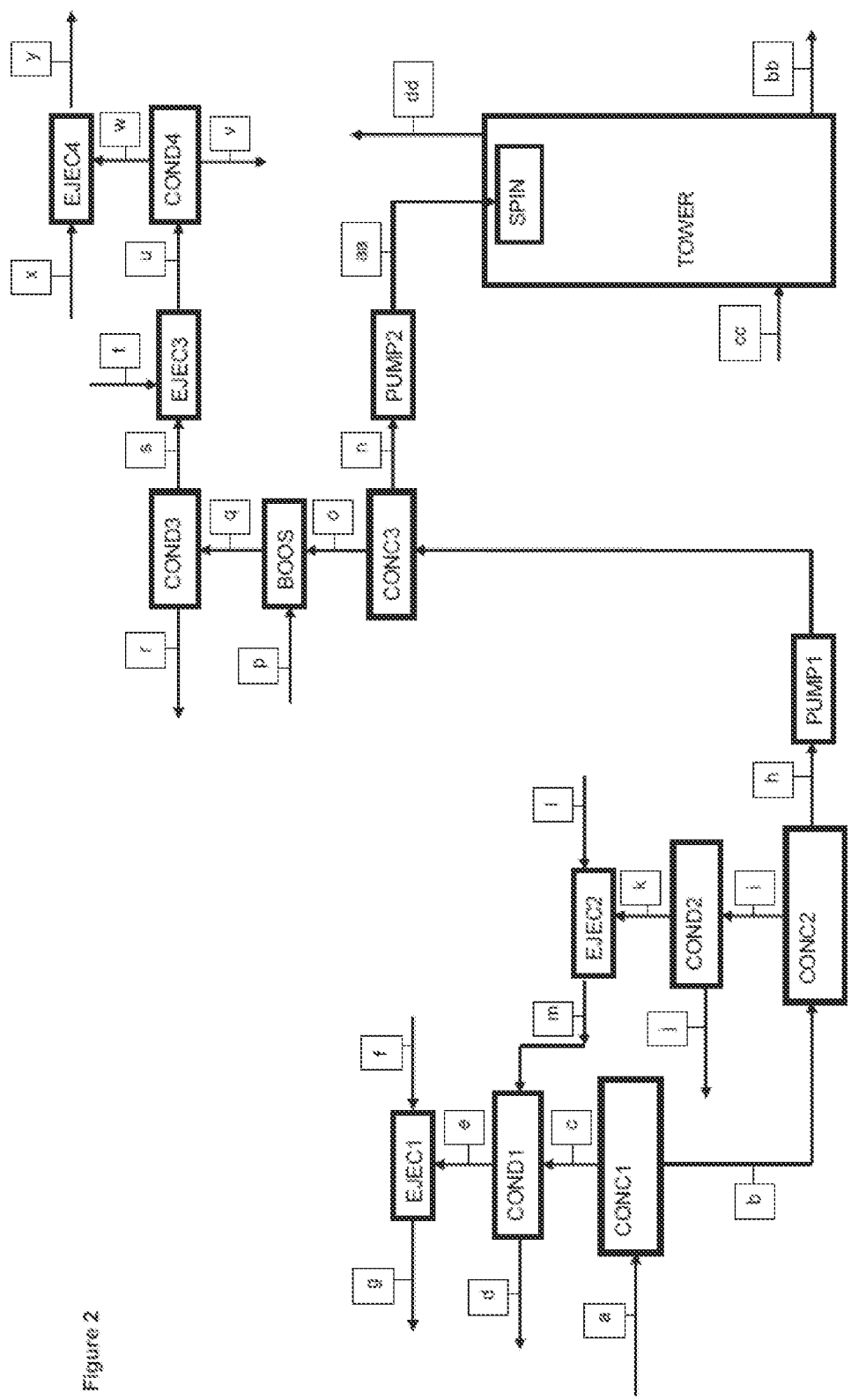
FIG. 2 is a schematic representation of an embodiment of the present invention.

In FIG. 2, one embodiment of the present invention is presented. Urea solution with a concentration of typically 50 to 75% by weight of urea and a temperature of typically 60 to 90° C. is added to a concentrator (CONC1) via line (a). The concentrator (CONC1) is a shell and tube heat exchanger and the urea solution is subjected to the tube side of said concentrator. At the shell side of said concentrator steam is added to heat the solution and to evaporate the volatile water fraction. The urea solution leaving the concentrator (CONC1) via line (b) has typically a temperature between 110 and 135° C. and a concentration between 87 and 95% by weight and preferably between 89 and 94% by weight. Said concentrator is operated at sub atmospheric pressure between 20 and 50 kPa. The formed vapor comprising water and small amounts of ammonia and carbon dioxide is discharging from said concentrator via line (c). Said vapor is condensed in a condenser (COND1) and leaves said condenser as process condensate via line (d). Non-condensed vapor is leaving said condenser via line (e) and is subjected to an ejector (EJEC1) to increase the pressure to atmospheric. The driving force for said ejector is usually steam added via line (f). The steam together with the non-condensed vapor leaves said ejector via line (g) and can be subjected to the atmosphere or is purified in the urea plant itself.

The urea solution leaving the concentrator (CONC1) is added to a next concentrator (CONC2) via line (b). The driving force to convey the urea solution from concentrator (CONC1) to concentrator (CONC2) can be done by the pressure difference between these concentrators, by using a pump or by the gravity flow.

The concentrator (CONC2) is a shell and tube heat exchanger and the urea solution is subjected to the tube side of said concentrator. At the shell side of said concentrator steam is added to heat the solution and to evaporate the volatile water fraction. The urea solution leaving the concentrator (CONC2) via line (h) has typically a temperature between 120 and 138° C. and a concentration between 94 and 99.5% by weight and preferably between 96 and 99% by weight. Said concentrator is operated at sub atmospheric pressure between 5 and 30 kPa. The formed vapor, comprising water and small amounts of ammonia and carbon dioxide, is discharging from said concentrator via line (i). Said vapor is condensed in a condenser (COND2) and leaves said condenser as process condensate via line (j). Non-condensed vapor is leaving said condenser via line (k) and is subjected to an ejector (EJEC2) to increase the pressure to atmospheric. The driving force for said ejector is usually steam added by line (1). The steam together with the non-condensed vapor leaves said ejector via line (m) and can be subjected to the atmosphere or is purified in the urea plant itself.

The urea solution leaving the concentrator (CONC2) is added to a next concentrator (CONC3) via line (h). The driving force to convey the urea solution from concentrator (CONC2) to concentrator (CONC3) can be done by using a pump (PUMP1). The concentrators (CONC1) and (CONC2) are located below the concentrator (CONC3). Moreover, the concentrator (CONC3) and associated condensers (COND3 and COND4) are located on the roof of the prilling tower (TOWER). It is also possible to locate only concentrator (CONC3) on the roof of the prilling tower, while placing the associated condensers (COND3) and (COND4) including ejectors below said concentrator (CONC3). This has an advantage that not all the bulky equipment associated with the third concentrator (CONC3) should be placed on the roof of the prilling tower, as only the location of the concentrator (CONC3) with respect to the prilling tower is critical.

The concentrator (CONC3) is a shell and tube heat exchanger and the urea solution is subjected to the tube side of said concentrator. At the shell side of said concentrator steam is added to heat the solution and to evaporate the volatile water fraction. The urea solution leaving the concentrator (CONC3) via line (n) has typically a temperature between 137 and 145° C. and a concentration between 99 and 99.9% by weight and preferably between 99.2 and 99.8% by weight. Said concentrator is operated at a sub-atmospheric pressure between 2 and 5 kPa. In said concentrator, heat is supplied and including the involved retention, the by-product biuret is formed. By that biuret reaction, ammonia is formed as well. Because of the sub-atmospheric condition in said concentrator, the formed ammonia escapes together with the formed water vapor the concentrator via line (o) to a small sized booster ejector (BOOS). The driving force for the booster ejector is steam supply via line (p). The boosted vapor leaving said booster ejector via line (q) is subjected to a condenser (COND3). The formed process condensate leaves said condenser via line (r) while the non-condensed vapor leaving said condenser via line (s) is subjected to an ejector (EJEC3). Also said ejector is driven by steam via line (t) and increases the pressure of the vapor leaving said ejector via line (u). This vapor is subjected to a next condenser (COND4) where the formed process condensate leaves said condenser via line (v) and the non-condensed inert vapor via line (w) is subjected to a next ejector (EJEC4). Also said ejector is driven by steam via line (x) and increases the pressure of the vapor discharging from said ejector to atmospheric pressure. That inert vapor is sent via line (y) into the atmosphere or is preferably purified from ammonia elsewhere in the urea plant. The process condensate that leaves said condensers is collected and furthermore processed in the urea plant to become clean process condensate.

The urea melt that leaves the concentrator (CONC3) via line (n) is conveyed to the sprayers or spinning basket at the top of the prilling tower via line (aa). The driving force to convey the urea solution from concentrator (CONC3) to the sprayers or spinning basket (SPIN) is preferably done by using a pump (PUMP2) but in certain occasions by gravity flow is possible. The distance between said concentrator and the spinning basket (SPIN) is less than 15 meters. Releasing the crystallization heat and cooling the formed crystallized product in the prilling tower (TOWER) is done by air supply via line (cc). Since the crystallization temperature of urea melt is between 130 and 133° C., dependent of the amount of water comprising in that melt, the melt line between the concentrator (CONC3) and the sprayers or spinning basket (SPIN) should be kept hot (130° C.). Therefore said urea melt transportation line (aa) is traced or jacketed. The heating agent for keeping the melt line hot is usually steam at a temperature of at least 130° C. Since the urea melt is kept at a temperature between 130 and 145° C. and the retention time in said urea melt line (aa) is only between 1 and 5 seconds, biuret is formed. Consequently ammonia is formed in that urea melt as well to an extent between 100 to 300 ppm of weight at the entrance of the sprayers or spinning basket (SPIN). When the urea melt is sprayed across the circumferential area of the prilling tower (TOWER) the ammonia concentration in the crystallized urea product leaving said prilling tower via line (bb) is only 25 to 150 ppm by weight. The difference of the ammonia concentrations in the urea melt leaving the sprayers or spinning basket (SPIN) and the ammonia concentration in the product via line (bb) is released into the air flow that is discharged from said prilling tower via line (dd). The amount of used air in the prilling tower (TOWER) necessary to release the crystallization heat and to cool down the crystallized product determines the ammonia concentration in the air discharging from said prilling tower via line (dd).

The invention claimed is:

1. A method for urea production in a urea production plant, comprising the steps of:
   (a) synthesizing urea from ammonia and carbon dioxide resulting in a urea solution,
   (b) concentrating the urea solution in at least three concentrating steps, yielding in a last step a urea melt, and
   (c) forming urea prills from the urea melt,
   wherein the residence time of the urea melt during transport between the last concentrating step in (b) and step (c) is less than 20 sec.

2. The method of claim 1, wherein said residence time is less than 10 sec.

3. The method of claim 1, wherein step (b) comprises three, four or five concentration steps.

4. A urea production plant comprising a urea synthesis section, a concentrating section and a prilling tower,
   which concentrating section comprises at least three concentrators including a last concentrator upstream of the prilling tower,
   wherein a urea melt transportation line connecting a urea melt outlet of the last concentrator with a urea melt inlet of the prilling tower is arranged such as to realise a residence time of urea melt in the transportation line of less than 20 sec.

5. The urea production plant according to claim 4, wherein the length of the urea melt transportation line is less than 60 m.

6. The plant according to claim 5, wherein said length is less than 40 m.

7. The plant according to claim 6, wherein said length is less than 20 m.

8. The plant according to claim 4, wherein the urea melt outlet of the last concentrator is at least 5 m higher than the urea melt inlet of the prilling tower in vertical height.

9. The plant according to claim 8, wherein the urea melt outlet of the last concentrator is at least 8 m higher than the urea melt inlet of the prilling tower in vertical height.

10. The plant according to claim 4, wherein the concentrating section comprises three, four or five concentrators.

11. A method for reducing ammonia emissions in a prilling tower of an existing urea production plant, wherein the existing plant comprises at least two existing concentrators and a prilling tower, said method comprising
    placing at least one additional concentrator between the prilling tower and the last concentrator immediately preceding the prilling tower wherein the last concentrator is at a level above the previous concentrators such that the length of the urea melt transportation line connecting a urea melt outlet of the additional concentrator with the urea melt inlet of the prilling tower is less than would be present if the last concentrator were at ground level.

12. The method according to claim 11, wherein one, two or three additional concentrators are placed between the existing concentrator and the prilling tower.

13. The method according to claim 11, wherein said length of the urea melt transportation line is less than 20 m.

14. The method according to claim 11, wherein the urea melt outlet of the last additional concentrator is at the same level or higher than the urea melt inlet of the prilling tower.

15. The method according to claim 11, wherein said last concentrator is at a level at the top of or above the prilling tower.

\* \* \* \* \*